United States Patent [19]

Brown et al.

[11] Patent Number: 5,583,014
[45] Date of Patent: Dec. 10, 1996

[54] **PREPARATION AND USE OF ENZYME-DETERGENT EXTRACTED *STREPTOCOCCUS ZOOPIDEMICUS* VACCINE**

[75] Inventors: Karen K. Brown, Kansas City, Mo.;
Sharon A. Bryant, Shawnee, Kans.;
Richard C. Stewart, Pensacola, Fla.;
Richard E. Parizek, Lenexa, Kans.

[73] Assignee: Bayer Corporation, Pittsburgh, Pa.

[21] Appl. No.: 547,733

[22] Filed: Jul. 3, 1990

[51] Int. Cl.⁶ .............. A61K 39/09; C12P 21/00; C12N 1/20
[52] U.S. Cl. .............. 435/71.2; 424/244.1; 435/71.1; 435/253.4; 435/713; 435/27.2; 435/885; 530/412; 530/806; 530/826
[58] Field of Search .............. 435/272, 253.4, 435/885, 71.2, 71.3; 424/92, 244.1; 530/412, 806, 826

[56] References Cited

U.S. PATENT DOCUMENTS 4,582,798  4/1986  Brown et al. .............. 424/92
4,977,082  12/1990  Boyle et al. .............. 435/253.4

OTHER PUBLICATIONS

Bergey's Manual of Determinitive Bacteriology, (8th Ed), p. 491, 1974.
Farrow et al., Biological Abstracts, vol. 80, No. 3, Abstract No. 18743, 1985.
*Bergey's Manual of Systematic Bacteriology*, vol. 2, p. 1049–1050, 1986.
Monsen et al., Chemical Abstracts, vol. 98, No. 13, Abstract No. 103894x, 1983.

*Primary Examiner*—David M. Naff
*Assistant Examiner*—Deborah K. Ware
*Attorney, Agent, or Firm*—Joseph C. Gil; Lyndanne M. Whalen; Godfried R. Akororli

[57] ABSTRACT

A vaccine effective against *S. zooepidemicus*-caused infections is made by enzymatic digestion of *S. zooepidemicus* and subsequent detergent treatment of the product of this digestion. The antigenic material thus obtained is then combined with an

PREPARATION AND USE OF ENZYME-DETERGENT EXTRACTED *STREPTOCOCCUS ZOOPIDEMICUS* VACCINE

BACKGROUND OF THE INVENTION

The present invention relates to a method for the preparation of an immunogenic protein material from *Streptococcus zooepidemicus* bacteria using an enzymatic digestion and detergent treatment and use of the material as a vaccine against *S. zooepidemicus* infection in equines.

*S. zooepidemicus* is classified as a Lancefield Group C Streptococcus. See, for example, Bergey's Manual of Determinitive Bacteriology (8th Ed.), p. 491 (1974). The organism is a recognized bacterial pathogen of horses and is known to colonize the upper respiratory tract, vaginal microflora and skin of horses. Among the disease conditions in which *S. zooepidemicus* has been implicated or established as the primary etiologic pathogen include endometritis, cervicitis, abortion, mastitis, pneumonia, abscesses and joint infection.

*S. zooepidemicus* is almost routinely a secondary invader in horses suffering from viral respiratory infections such as equine influenza. This secondary infection may consist of upper respiratory invasion of the sinuses, eustachian tubes or gluttural pouches resulting in a mucoprurulent nasal exudate, persistent fever or lymphadenitis. The incidence of respiratory infections caused by streptococci is quite high in horses but organisms isolated from infected horses are seldom identified as to species. This lack of identification makes accurate estimation of the incidence of *S. zooepidemicus*-caused infections difficult. However, it is believed that this organism may be the most prevalent of streptococci affecting horses.

*S. zooepidemicus* is the bacterial pathogen most often isolated from cases of foal pneumonia, and in adult horses, is recognized as the most common etiologic agent involved in pneumonic disease. *S. zooepidemicus* also appears to be a major cause of abortion in horses and has been estimated to cause between ten and twenty percent of all equine abortions. The majority of internal and external abscesses in horses result from *S. zooepidemicus*.

At the present time, *S. zooepidemicus* is treated with antibiotics such as penicillin, tetracycline or gentamicin. However, resistant strains appear to be on the increase. To date, there has been no effective prophylactic agent developed to protect animals from *S. zooepidemicus* infection.

SUMMARY OF THE INVENTION

It is an object of the present invention to provide a vaccine effective against *S. zooepidemicus*-caused infections.

It is another object of the present invention to provide a method for making a vaccine effective against *S. zooepidemicus*-caused infections.

It is a further object of the present invention to provide an immunogenic protein material obtained from *S. zooepidemicus*.

These and other objects which will be apparent to those skilled in the art are accomplished by enzymatic digestion of *S. zooepidemicus* and a subsequent detergent treatment of the product of this digestion process.

DETAILED DESCRIPTION OF THE INVENTION

In the practice of the present invention, a vaccine is prepared by extracting an M-like protein from the cell wall of *S. zooepidemicus* organisms by lytic enzyme digestion followed by treatment with an anionic detergent. The resulting M-protein extract can then be used to prepare a vaccine capable of protecting animals from *S. zooepidemicus* infection.

The purification of similar "M-like proteins" from *Streptococcus equi* is described in an article by J. B. Woolcock, Infect. and Immun., July, 1974, p. 116–122 and in our U.S. Pat. No. 4,582,798. As used herein, the expression "M-like protein" means the immunogenic protein(s) of the *S. zooepidemicus* organism which appears similar in molecular weight and activity to the M-protein of group A streptococci. It has now been found that an effective vaccine against *S. zooepidemicus*-caused infections may be prepared from an M-protein extract of *S. zooepidemicus* which has been extracted in substantially the same manner as the *Streptococcus equi* antigen described in our U.S. Pat. No. 4,582,798.

The antigenic M-like protein can be efficaciously removed from a *S. zooepidemicus* culture in a two step process using lytic enzyme digestion followed by treatment with an anionic detergent and that this extract can be used to prepare a vaccine effective in immunizing horses against infection by *S. zooepidemicus.* The potency of this antigen preparation has been determined using the method disclosed in U.S. Pat. No. 4,529,581, entitled, Determining Potency of Streptococcal Preparations, and has been confirmed in a rabbit challenge study, described herein.

The procedure for our enzymatic extraction of Streptococcal M-like protein involves growth of a Streptococcal culture under growth-inducing conditions (e.g. at 37° C. in a suitable media) followed by concentration of the cells (e.g. by centrifugation or filtration). The cell concentrate is either diluted or washed in a suitable buffer. A bacteriolytic enzyme such as mutanolysin is then added to the cell concentrate and incubated at sufficient temperature and time for enzymatic lysis of part of the cell wall. Partial lysis means lysis sufficient to make the M-protein available for subsequent detergent extraction but without deleterious effect on the M-protein. In general, we found this can be accomplished by exposing the *S. zooepidemicus* culture to the lytic enzyme at 37° C. for no more than about 24 hours at an enzyme concentration of about 1–10 units per ml of original culture volume. An anionic detergent such as sodium lauryl sulfate or dioctyl sodium sulfosuccinate is then added to the cell concentrate and allowed to incubate to complete the *S. zooepidemicus* cell extraction treatment. Cells and cell debris are then removed by centrifugation or filtration and the final cell-free antigen solution sterilized by filtration or chemical treatment. The cell-free antigen solution is immunogenic and useful in immunizing horses against infection by *S. zooepidemicus* organisms and has the following characteristics: a molecular weight ranging from about 25,000 to about 75,000 daltons, preferably from about 30,000 to about 66,000 daltons as determined by gel electrophoresis; heat stability to about 121° C., preferably to about 100° C.; and trypsin sensitivity.

Any of the known bacteriolytic enzymes may be used in the practice of the present invention but the preferred bacteriolytic enzyme is mutanolysin (N-acetylmuramidase) which may be obtained from the culture filtrate of *Streptomyces globisporus* and which is commercially available from Sigma Chemical Co., St. Louis, Mo. 63178 and Dainippon Pharmaceutical Co., Ltd., Osaka, Japan. Studies using mutanolysin as a method of lysing Streptococcal cell walls have been conducted for purposes other than M-like protein retrieval. Reports of these studies have been written by K.

Yohagawa et al in Antimicrobial Agents and Chemotherapy, August, 1974, p. 156–165, G. B. Calandar and R. M. Cole in Infect. and Immun., June, 1980, p. 1033–1037, and B. I. DeCueninck et al., in Infect. and Immun., February, 1982, p. 572–582. Mutanolysin and other bacteriolytic enzymes (glycosidases) such as egg white lysozyme are thought to act on linear sequences of N-acetylglucosamines and N-acetyl muramic acid residues of the bacterial cell walls.

Any *S. zooepidemicus* isolate may be used in the practice of the present invention. The *S. zooepidemicus* isolate used in the Examples reported herein which has been designated isolate #127 was obtained from an infected horse on a farm in DeSoto, Kansas. This isolate was characterized as *S. zooepidemicus* using the fermentation technique described in Bergey's Manual of Determinative Bacteriology at pages 491, 498. (8th Ed.). This isolate did not exhibit any properties or characteristics which indicated that it differed in any significant way from the textbook description and properties of *S. zooepidemicus*.

In the practice of the present invention the *S. zooepidemicus* isolate may be grown in any suitable growth medium. The chemically defined medium described by I. van de Rijn in Infect. and Immun., 27: 444–448, 1980 (hereinafter referred to as "van de Rijn's medium") is particularly preferred.

This medium is prepared from the following components in the amounts indicated:

| Group 1 | |
|---|---|
| $FeSO_4.7H_2O$ | 5 mg/l |
| $Fe(NO_3)_2.9H_2O$ | 1 mg/l |
| $K_2HPO_4$ | 200 mg/l |
| $KH_2PO_4$ | 1000 mg/l |
| $MgSO_4.7H_2O$ | 700 mg/l |
| $MnSO_4$ | 5 mg/l |
| Group 2 | |
| DL-Alanine | 100 mg/l |
| L-Arginine | 100 mg/l |
| L-Aspartic Acid | 100 mg/l |
| L-Cystine | 50 mg/l |
| L-Glutamic Acid | 100 mg/l |
| L-Glutamine | 200 mg/l |
| Glycine | 100 mg/l |
| L-Histidine | 100 mg/l |
| L-Isoleucine | 100 mg/l |
| L-Leucine | 100 mg/l |
| L-Lysine | 100 mg/l |
| L-Methionine | 100 mg/l |
| L-Phenylalanine | 100 mg/l |
| L-Proline | 100 mg/l |
| Hydroxy-L-proline | 100 mg/l |
| L-Serine | 100 mg/l |
| L-Threonine | 200 mg/l |
| L-Tryptophan | 100 mg/l |
| L-Tyrosine | 100 mg/l |
| L-Valine | 100 mg/l |
| Group 3 | |
| p-Aminobenzoic acid | 0.2 mg/l |
| Biotin | 0.2 mg/l |
| Folic Acid | 0.8 mg/l |
| Niacinamide | 1.0 mg/l |
| β-Nicotineamide adenine dinucleotide | 2.5 mg/l |
| Pantothenate calcium salt | 2.0 mg/l |
| Pyridoxal | 1.0 mg/l |
| Pyridoxamine dihydrochloride | 1.0 mg/l |
| Riboflavin | 2.0 mg/l |
| Thiamine hydrochloride | 1.0 mg/l |
| Vitamine $B_{12}$ | 0.1 mg/l |
| Group 4 | |
| Glucose | 10,000.0 mg/l |
| Group 5 | |
| Adenine | 20 mg/l |
| Guanine hydrochloride | 20 mg/l |
| Uracil | 20 mg/l |
| Group 6 | |
| $CaCl_2.6H_2O$ | 10 mg/l |
| $NaC_2H_3O_2.3H_2O$ | 4,500 mg/l |
| L-Cysteine | 500 mg/l |
| $NaHCO_3$ | 2,500 mg/l |
| $NaH_2PO_4.H_2O$ | 3,195 mg/l |
| $NaH_2PO_4$ | 7,350 mg/l. |

The above-listed components were added in groups. Each group was dissolved completely before addition of the next. The purines and pyrimidines of Group 5 were dissolved in 2N HCl at 500×concentration and diluted to 100×with distilled water before use or storage at −20° C. Each component in Group 6 was added separately. The final pH of the medium was between 6.95 and 7.05. The isolate is maintained in the growth medium at a temperature of from about 34° C. to about 38° C., preferably from about 35° C. to about 37° C. and most preferably about 37° C. for a period of from about 6 to about 24 hours, preferably from about 12 to about 18 hours and most preferably about 16 hours.

The *S. zooepidemicus* cells may then be concentrated, preferably from about 10 to about 50 fold by any of the techniques known to those skilled in the art. One particularly preferred concentration technique is cross-flow filtration. The cells are then washed by addition of a buffer solution having a pH of from about 6.0 to about 7.0, preferably from about 6.3 to about 6.7. A 0.1M Trizma(2-amino-2-hydroxymethyl-1,3-propanediol)-HCl buffer with a pH adjusted to 6.5 with NaOH is one of the preferred buffer solutions.

The bacteriolytic enzyme is then added to the washed cells, preferably in the form of a solution having a concentration of at least 1000 units/ml, preferably at least 4000 units/ml. In a preferred embodiment of the invention, a 5,000 unit/ml solution of mutanolysin is added to the concentrated cells. The bacteriolytic enzyme is added until a final enzyme concentration of from about 1 to about 10, preferably from about 3 to about 7, and most preferably about 5 units per ml original culture volume is achieved. This mixture is then incubated at a temperature of from about 30° C. to about 40° C., preferably from about 35° to about 37° C. and most preferably 37° C. for from about 12 to about 24 hours, preferably from about 14 to about 18 hours and most preferably 16 hours.

An anionic detergent is then added, preferably in the form of a solution having a concentration of from about 1% to about 20%, preferably from about 10% to about 15%. The anionic detergent is added in a quantity such that the concentration of detergent in the final solution is from about 0.01% to about 0.10%, preferably from about 0.03% to about 0.07%. Any of the known anionic detergents may be used. Examples of suitable anionic detergents include sodium lauryl sulfate and dioctyl sodium sulfosuccinate. Preferred anionic detergents are sodium lauryl sulfate and dioctyl sodium sulfosuccinate. In a preferred embodiment of the invention, a 10% sodium lauryl sulfate solution is added to the at least partially lysed product until a final concentration of about 0.05% is obtained. This detergent-containing solution is then incubated at a temperature of from about 30° C. to about 40° C., preferably from about 35° C. to about 38° C., most preferably about 37° C. for a period of from about 10 to about 60 minutes, preferably from about 20 to about 45 minutes, most preferably about 30 minutes.

The S. zooepidemicus cells and cell debris are then removed from the solution by any of the techniques known to those skilled in the art. Two of the particularly preferred techniques for removing the S. zooepidemicus cells and cell debris are cross flow filtration and centrifugation. The remaining effluent (i.e., the antigenic material) may then be sterilized by any of the sterilization techniques known to those skilled in the art. In one particularly preferred technique, the effluent is passed through a 0.2 micron filter and held at a temperature of from about 4° C. to about 10° C., preferably from about 4° C. to about 7° C., most preferably about 4° C.

The M-protein extract thus recovered may then be combined with an appropriate adjuvant to prepare the final vaccine. Suitable adjuvants include Carbopol, aluminum hydroxide, aluminum sulfate and Drakeol. Preferred adjuvants are Carbopol-based adjuvants using Carbopol 934P.

Having thus described our invention in detail, the following examples are given as being illustrative thereof. Unless otherwise indicated, all percentages given in these examples are percents by weight.

EXAMPLES

Example 1

A vaccine was prepared by growing S. zooepidemicus isolate #127 in van de Rijn medium for 16 hours at 37° C., concentrating the S. zooepidemicus 40-fold using cross-flow filtration, washing the cells with 0.1M Trizma-HCl buffer solution having a pH of 6.5, adding a 5,000 unit/ml solution of mutanolysin until an enzyme concentration of 5 units per ml original culture volume was obtained and incubating the resultant mixture for 16 hours at 37° C., adding 10% sodium lauryl sulfate to a concentration of 0.05% and incubating at 37° C. for 30 minutes, centrifuging the mixture, filtering the effluent through 0.2 micron filter and combining the recovered extract with a Carbopol-based adjuvant called Havlogen in the manner described in the DETAILED DESCRIPTION OF THE INVENTION portion of this specification. This vaccine was then tested in rabbits to determine its immunizing capabilities. The vaccine was tested against another vaccine made from S. zooepidemicus M-protein extract obtained by the hot acid extraction known to those skilled in the art.

The comparative vaccine was made by using part of the same 40-fold concentrated S. zooepidemicus culture, washing the cells with phosphate buffered saline, adjusting the pH of the washed cell suspension to a pH of 2.0 with HCl and maintaining the resultant mixture at a temperature of 95° C. for 15 minutes. The mixture was then centrifuged. The cell free supernate thus obtained was then combined with the same Carbopol-based adjuvant used to prepare the vaccine within the scope of the present invention.

The rabbit challenge was conducted by vaccinating groups of eight to ten rabbits intramuscularly twice (at three week intervals) with 1 ml of either the vaccine of the present invention prepared by mutanolysin M protein extraction or hot acid M protein extracted vaccine. Ten additional rabbits were unvaccinated to serve as controls. Two weeks after the second inoculation, all rabbits were challenged with 2 ml of virulent log phase S. zooepidemicus isolate #127 by intraperitoneal injection. One half of the rabbits in each group were challenged with a $10^{-4}$ dilution of isolate 127 and the other half were challenged with a $10^{-5}$ dilution (approximately $10^4$ to $10^5$ organisms per rabbit). The rabbits were observed for 7 days after challenge and the number of deaths recorded. The results of this study are summarized in the following table.

TABLE 1

| VACCINE | CHALLENGE DILUTION | SUR-VIVORS/ TOTAL | CUMMU-LATIVE SUR-VIVORS/ TOTAL | % PRO-TECT |
|---|---|---|---|---|
| Mutanolysin-extracted M-protein | $10^{-4}$ $10^{-5}$ | 3/4 4/4 | 7/8 | 87.6% |
| Hot Acid extracted M-protein | $10^{-4}$ $10^{-5}$ | 2/5 3/5 | 5/10 | 50.0% |
| Unvaccinated Controls | $10^{-4}$ $10^{-5}$ | 0/5 0/5 | 0/10 | 0.0% |

The results presented in Table 1 clearly show that the mutanolysin extract vaccine gave greater protection than hot acid extract vaccine. These data also indicate that the mutanolysin extract vaccine is capable of protecting animals from virulent S. zooepidemicus infections.

Example 2

The mutanolysin extract and hot acid extract vaccines tested in Example 1 were further tested for potency against S. zooepidemicus in horses by the method for determining potency of Streptococcal infections disclosed in U.S. Pat. No. 4,529,581. More specifically, three different known positive horse sera were each mixed with an equal volume of either a vaccine or control of known dilution and allowed to incubate at 4°–7° C. for 1 hour. 5.0 ml of the mutanolysin extract vaccine prepared in Example 1 or hot acid extract vaccine prepared in Example 1 or a phosphate buffered saline solution (the control) were combined with 5.0 ml of the horse serum in each of three test series. The test series were designated #972, #973 and #980. The antibodies present in the horse sera combine with antigen if specific sites are present. The mixtures were then centrifuged to remove antigen-antibody complexes to prevent interference in the test. The remaining soluble antibodies were then incubated with a known lethal mouse challenge of S. zooepidemicus (i.e., $LD_{50}$ $10^{6.5}$–$10^{8.0}$ diluted in Todd Hewitt Broth) to neutralize all or a portion of the lethal challenge at a temperature of 4°–7° C. for 1 hour. The extent of neutralization achieved will, of course, depend upon the amount of soluble antibody present. Each of the neutralized or partially neutralized mixtures is then used to inoculate mice to determine the $LD_{50}$ value in accordance with techniques known to those in the art. The antigenicity of the vaccine is measured by the increase in $LD_{50}$ over the $LD_{50}$ of the Antiserum Control. The greater this increase in $LD_{50}$, the greater the antigenicity of the vaccine. Table 2 shows the results of vaccines tested via this assay.

In Table 2, the term CPU means combining power unit and was calculated by Log of $LD_{50}$ of vaccine+horse serum+ S. zooepidemicus—Log of $LD_{50}$ of control+horse serum+S. zooepidemicus=CPU.

The CPU value indicates whether the antigen being tested will combine with protective antibody to S. zooepidemicus in the horse sera. If it does combine, the antigen will be useable in a vaccine, i.e., it will raise the protective antibody to S. zooepidemicus in horses. Whether the antigen combines with the protective antibodies in the horse sera can be determined by the effect addition of antigen to the horse serum has on the lethality ($LD_{50}$) in mice when the horse serum is combined with live bacteria and injected into mice. If the antigen binds with the antibodies, more mice die (i.e., the $LD_{50}$ goes up) because the antibodies are not available to protect the mice against the live bacteria. The increase in the $LD_{50}$ value of the antigen-containing samples as compared to the $LD_{50}$ value of the Control is reflected in the CPU. The higher the CPU, the better the antigen for purposes of vaccine preparation.

The data presented below in Table 2 clearly indicate that the antigens produced in accordance with the present invention are useful for the production of a vaccine against *S. zooepidemicus* infections.

TABLE 2

| MOUSE COMBINING POWER RESULTS OF VACCINE PREPARATION | | | |
| --- | --- | --- | --- |
| TEST SERIES | EXTRACTANT | $LD_{50}$ | CPU |
| 972 | Hot Acid | $10^{6.6}$ | 2.8 |
|  | Mutanolysin | $10^{7.7}$ | 3.9 |
|  | Control | $10^{3.8}$ | — |
| 973 | Hot Acid | $10^{6.6}$ | 2.8 |
|  | Mutanolysin | $10^{6.4}$ | 2.6 |
|  | Control | $10^{3.8}$ | — |
| 980 | Hot Acid | $10^{7.5}$ | 2.0 |
|  | Mutanolysin | $10^{8.5}$ | 3.0 |
|  | Control | $10^{5.5}$ | — |

EXAMPLE 3

Various dilutions of the mutanolysin extract vaccine were tested in the same manner described in Example 2. The results of these tests are given in Table 3. The dilutions reported in this Table are given in terms of volume/volume.

TABLE 3

| TEST SERIES | EXTRACTANT | ANTIGEN DILUTION | $LD_{50}$ | CPU |
| --- | --- | --- | --- | --- |
| 972 | Mutanolysin | Undil. | $10^{8.3}$ | 3.3 |
|  |  | 1:2 | $10^{5.8}$ | 0.8 |
|  |  | 1:5 | $10^{6.3}$ | 1.3 |
|  | Control | — | $10^{6.3}$ | — |
| 973 | Mutanolysin | Undil. | $10^{7.3}$ | 2.6 |
|  |  | 1:2 | $10^{6.4}$ | 1.7 |
|  |  | 1:5 | $10^{5.8}$ | 1.1 |
|  | Control | — | $10^{4.7}$ | — |

These data clearly show that dilution of the antigenic material decreases the $LD_{50}$ and CPU values of the vaccine.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of preparing a cell-free antigenic solution useful in immunizing horses against *S. zooepidemicus* bacteria, the method comprising the steps of:

(a) growing *S. zooepidemicus* bacteria under growth inducing conditions;

(b) adding mutanolysin enzyme to the bacteria of step (a);

(c) incubating the bacteria of step (b) under conditions such that M-like protein becomes available for detergent extraction without deleterious effect on the M-protein;

(d) adding an anionic detergent to the product of step (c) to extract immunogenic M-like protein into a supernate;

(e) separating the soluble extracted M-like protein supernate from bacterial cells and cell debris; and (f) sterilizing the soluble M-like protein supernate product of step (e).

2. The method of claim 1 wherein the enzyme exposure of step (b) is at 37° C. for not more than about 24 hours at an enzyme concentration of 1–10 units per ml of original culture volume.

3. The method of claim 1 wherein the detergent of step d is sodium lauryl sulfate and the exposure is at 37° C. for not more than about 60 minutes at a detergent concentration of 0.01–0.10% by volume.

4. The method of claim 1 wherein the sterilization of step (f) is by filtration through a 0.2 micron filter.

5. The method of claim 1 wherein the enzyme of step (b) is mutanolysin, the detergent of step (d) is sodium lauryl sulfate, and the sterilization of step (f) is by filtration through a 0.2 micron filter.

\* \* \* \* \*